(12) United States Patent
Caplan et al.

(10) Patent No.: US 7,539,530 B2
(45) Date of Patent: May 26, 2009

(54) METHOD AND SYSTEM FOR SPECTRAL EXAMINATION OF VASCULAR WALLS THROUGH BLOOD DURING CARDIAC MOTION

(75) Inventors: Jay D. Caplan, Belmont, MA (US); Barbara J. Marshik-Geurts, Methuen, MA (US)

(73) Assignee: InfraReDx, Inc., Burlington, MA (US)

( * ) Notice: Subject to any disclaimer, the term of this patent is extended or adjusted under 35 U.S.C. 154(b) by 830 days.

(21) Appl. No.: 10/646,271

(22) Filed: Aug. 22, 2003

(65) Prior Publication Data

US 2005/0043637 A1 Feb. 24, 2005

(51) Int. Cl.
*A61B 6/00* (2006.01)
(52) U.S. Cl. ...................... 600/476; 600/473
(58) Field of Classification Search ................. 600/326, 600/407, 463, 481
See application file for complete search history.

(56) References Cited

U.S. PATENT DOCUMENTS

| | | | | |
|---|---|---|---|---|
| 5,217,456 | A * | 6/1993 | Narciso, Jr. .................. 606/15 |
| 5,383,467 | A * | 1/1995 | Auer et al. .................. 600/342 |
| 5,647,359 | A * | 7/1997 | Kohno et al. ................. 600/341 |
| 5,752,518 | A * | 5/1998 | McGee et al. ................ 600/424 |
| 6,272,376 | B1 | 8/2001 | Marcu et al. ................. 600/477 |
| 6,475,159 | B1 | 11/2002 | Casscells et al. ............. 600/549 |
| 6,485,413 | B1 | 11/2002 | Boppart et al. .............. 600/160 |
| 6,512,936 | B1 | 1/2003 | Monfre et al. ............... 600/322 |
| 6,512,937 | B2 | 1/2003 | Blank et al. ................. 600/322 |
| 6,658,278 | B2 | 12/2003 | Gruhl |
| 2002/0163622 | A1 | 11/2002 | Magnin et al. |
| 2004/0024298 | A1* | 2/2004 | Marshik-Geurts et al. ... 600/326 |

FOREIGN PATENT DOCUMENTS

WO WO 98/18388 A1 5/1998
WO WO 03/104864 A1 12/2003

OTHER PUBLICATIONS

International Preliminary Report on Patentability from International Patent Application PCT/US2004/027168, filed Aug. 20, 2004.

* cited by examiner

*Primary Examiner*—Eric F Winakur
*Assistant Examiner*—Michael T Rozanski
(74) *Attorney, Agent, or Firm*—Houston Eliseeva, LLP

(57) ABSTRACT

A method for improving the treatment and/or examination of vessel walls through fluid, such as blood, functions by identifying the points in time when the catheter is closest to the vessel wall or farthest from the vessel wall. Identification of this relative location enables improved spectral readings in larger vessels. In short, instead of trying to overcome motion (e.g., by centering the catheter), this approach takes advantage of motion by identify times when the catheter is closer to the vessel wall, in order to gather more useful spectral information or improve the efficacy of the treatment of the vessel walls. In the specific example, the invention is used for near infrared (NIR) spectroscopy. In some embodiments, the catheter head is designed to induce relative movement between the head and the vessel walls.

62 Claims, 9 Drawing Sheets

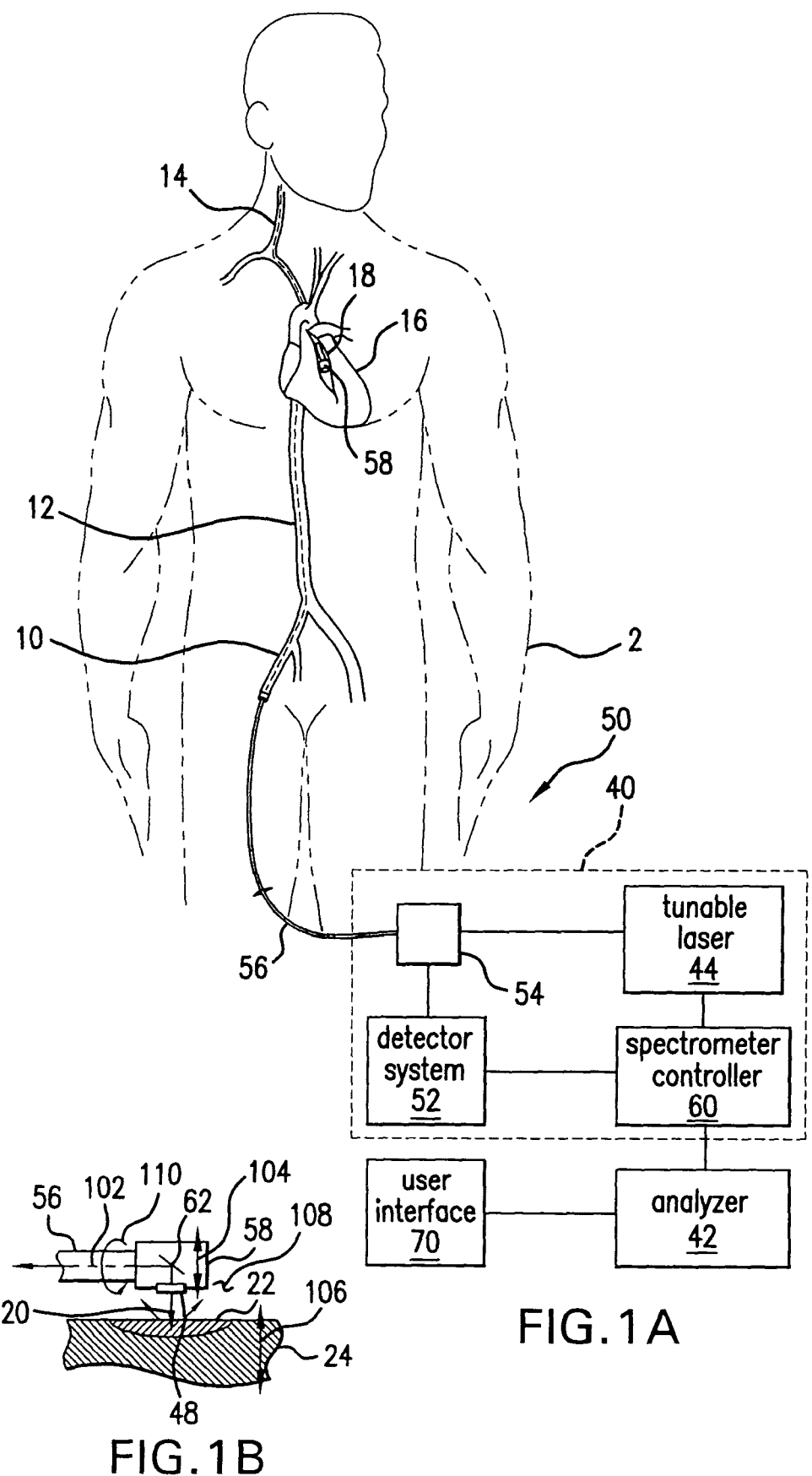

METHOD AND SYSTEM FOR SPECTRAL EXAMINATION OF VASCULAR WALLS THROUGH BLOOD DURING CARDIAC MOTION

BACKGROUND OF THE INVENTION

Probe-based, such as catheter-based, optical systems are applicable to a number of diagnostic and therapeutic medical applications. Optical coherence tomography is used to provide spatial resolution, enabling the imaging of internal structures. Spectroscopy is used to characterize the composition of structures, enabling the diagnosis of medical conditions, by differentiating between cancerous, dysplastic, and normal tissue structures, for example. Ablation systems are used to remove or destroy structures within the body to address various diseases, such as tachycardias, tumors, and coronary artery disease, in another example of a probe-based optical system.

For example, in one specific spectroscopic application, an optical source, such as a tunable laser, is used to access or scan a spectral band of interest, such as a scan band in the near infrared or 750 nanometers (nm) to 2.5 micrometers (μm). The generated light is used to illuminate tissue in a target area in vivo using the catheter. Diffusely reflected light resulting from the illumination is then collected and transmitted to a detector system, where a spectral response is resolved. The response is used to assess the state of the tissue.

This system can be used to diagnosis atherosclerosis, and specifically identify atherosclerotic lesions or plaques. This is an arterial disorder involving the intimae of medium- or large-sized arteries, including the aortic, carotid, coronary, and cerebral arteries.

Diagnostic systems based on Raman and fluorescence based schemes have also been proposed. Other wavelengths, such as visible, have also been suggested.

The environment in which the spectra are collected, however, creates problems. Due to the presence of intervening fluid, such as blood in the case of probes inserted into blood vessels, the spectral signals related to the properties of the tissue are overwhelmed. Thus, more complicated methods such as chemometrics are used to extract the spectra of the vessel walls in the presence of noise from blood, for example.

Chemometrics is the science of relating measurements made on a chemical system or process to the state of the system via application of mathematical or statistical methods. It can be used to predict the properties, such as chemical composition, of structures based on their spectral response. Mathematical manipulations such as linear regression of the spectral band of interest and classic least squares and inverse least squares and other multivariate analysis tools are available for building quantitative calibrations as well as qualitative models for discriminant analysis.

SUMMARY OF THE INVENTION

The treatment and/or analysis of vessel walls through blood, however, are complicated further by the fact that the physical relationship between the probe, and typically the probe head, and the blood vessel walls is poorly controlled. Thus, in diagnostic applications, such as spectroscopy applications, the unknown pathlength will affect the degree to which the detected spectrum is dominated by unwanted signal sources, such as blood, thus making it difficult to isolate the spectral response of the vessel walls or other structures of interest.

Moreover, the position of the catheter can vary in relation to the vessel wall over time. This is typically due to blood flow, respiratory motion, and cardiac motion. Therefore the amount of blood between the probe and the vessel wall varies over time and the contribution of the vessel wall to the collected information, such as spectra, varies correspondingly. The problem is further complicated in large vessels since the catheter head can be so far from the vessel walls that it is impossible to acquire any useful information.

One approach to addressing the influence of motion is electrocardiographic gating (ECG gating), where some preselected segment of the cardiac cycle is used for taking measurements. ECG gating can enable spectral acquisition during a period of lesser movement, or may reduce the variance in the distance between the vessel and the catheter head between samples by collecting information at the some specified point in the cycle over multiple cardiac cycles. ECG gating, however, has had limited success due to the weak correlation between vessel motion and catheter motion.

A second approach to reducing the influence of motion is the removal of blood from the field of view, either by replacing the blood with some other fluid or by occluding the blood flow in the area of measurement. These approaches are clinically undesirable, however. A related solution is to center the catheter in the vessel. Among other problems, this may cause all signals to be poor in a large vessel, due to the large catheter-to-vessel distance, however.

The present invention concerns an approach for improving the treatment and/or examination of vessels walls through fluid, such as blood. In the specific example, the invention is used for near infrared (NIR) spectroscopy. The invention can take advantage of the probe, such as catheter head, motion by identifying the points in time when the head is closest to the vessel wall or farthest from the vessel wall. Identification of this relative location enables meaningful spectral readings in larger vessels. In short, instead of trying to overcome motion (e.g., by centering the catheter), this approach takes advantage of motion by identify times when the catheter is closer to the vessel wall, in order to gather more useful spectral information or improve the efficacy of the treatment of the vessel walls.

In general, according to one aspect, the invention features a method for optically examining blood vessel walls with a probe through intervening fluid. The method comprises receiving an optical signal from the vessel walls through the intervening fluid at a head of a probe. The optical signal is then analyzed to determine whether the probe is close enough to the vessel wall to enable treatment or assessment of the vessel wall. The received optical signals are then used to assess the vessel walls or treatment initiated, depending upon whether the probe head is determined to be close enough to the vessels walls to enable the assessment or treatment of the vessel walls.

In the preferred embodiment, the optical signals are emitted from the probe and the step of receiving the optical signals comprises receiving the returning optical signals. In one embodiment, the step of analyzing the optical signals comprises determining amplitudes of the optical signals. The assessment of the vessel walls is performed based on a comparison of the optical signals to a threshold. Typically, the amplitude of the received optical signals is higher, and absorbance lower, when the probe is closer to the vessel walls. The vessels walls are assessed in response to their spectral response.

In another embodiment, the step of analyzing the optical signals comprises assessing the optical signals with respect to an expected spectral response of the intervening fluid and/or vessel walls. In one example, the assessment can be in the form of a simple spectral comparison. In another example, the assessment can be in the form of the application of a chemometric type model that is used as a filter to assess the spectra to determine whether they are more like the intervening fluid, such as blood spectra, or the tissue of interest. The step of using the received optical signal to assess the vessel walls is performed if the optical signal is poorly correlated to the spectral response of the intervening fluid, or blood.

In general, according to another aspect, the invention features a method for examining blood vessel walls with a probe through intervening fluid. This includes receiving an optical signal from the vessel walls, through the intervening fluid, at a head of the probe. The optical signal is then analyzed to determine the degree to which the received optical signal is characteristic of the vessel walls or intervening fluid. The received optical signal is then used to assess the vessel walls depending on the degree to which the optical signal is characteristic of those vessel walls.

The present invention is also directed techniques for inducing movement or desired movement characteristics in the probe or catheter heads through the design of the head.

In general according to one aspect, the invention features a probe for insertion into blood vessels. The probe comprises a head that induces movement relative to walls of the blood vessel.

In one embodiment, the head rotates and comprises an eccentric mass that induces the relative movement between the head and the walls of the blood vessel due to the rotation of the catheter head.

In other examples, the head is shaped to interact with flowing blood to move the head into proximity with or relative to the walls of the blood vessel. Fins can be used for this purpose, and cardiac gating can be employed to control signal acquisition.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1A is a schematic block diagram illustrating a catheter-based medical optical system to which the inventive system for compensating for catheter or cardiac motion is applicable;

FIG. 1B is a cross-sectional view of the catheter head positioned adjacent tissue illustrating the operation of the system and its motion;

FIG. 3A is a flow diagram showing a method for blood vessel analysis according to an embodiment of the present invention that assesses whether the collected spectrum is blood-like;

DETAILED DESCRIPTION OF THE PREFERRED EMBODIMENTS

Figure 1C:
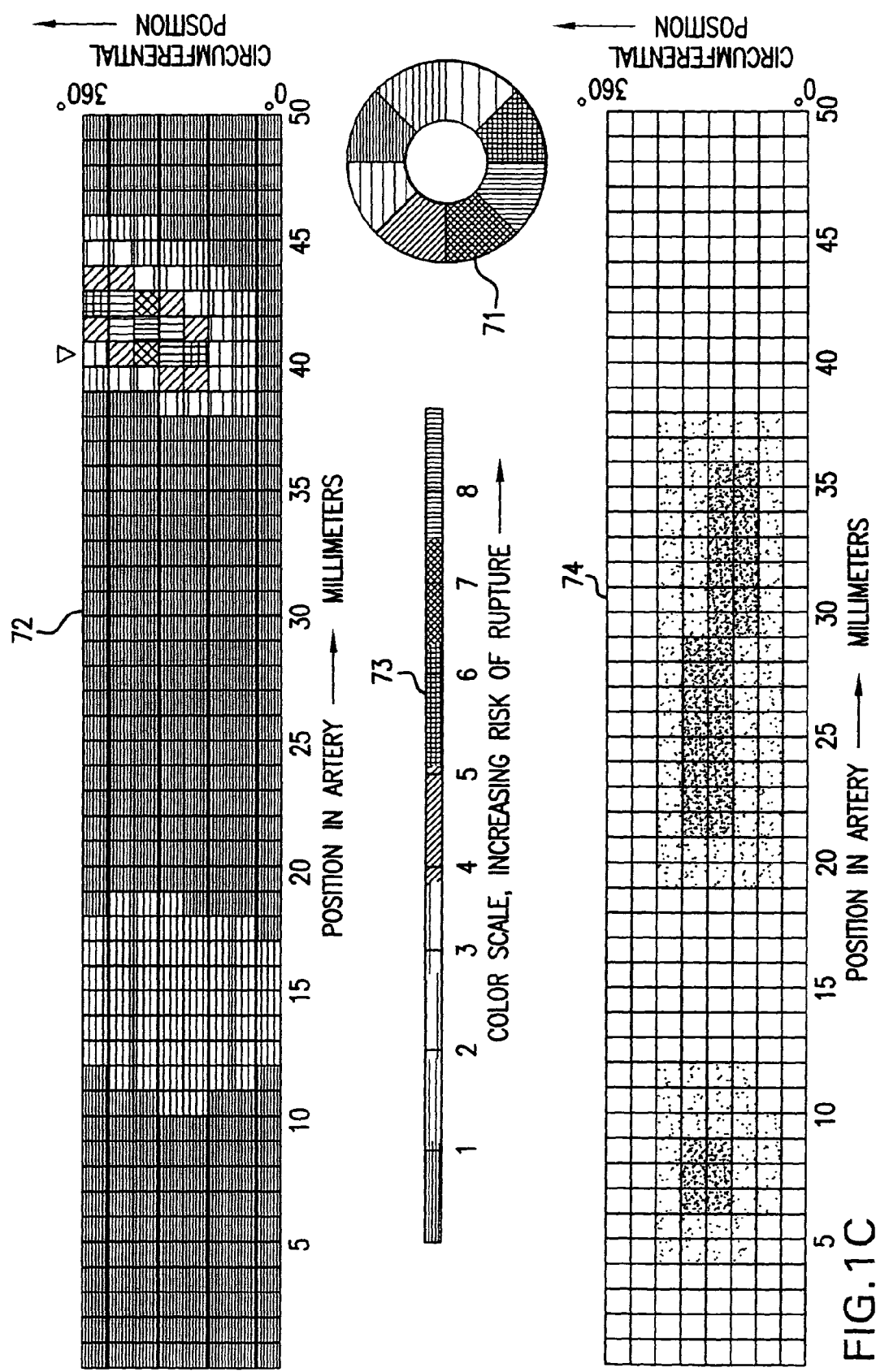
FIG. 1C is a schematic diagram of an image generated by the systems' user interface.

FIG. 1A shows an optical spectroscopic catheter system 50 for blood vessel analysis, to which the present invention is applicable, in one embodiment.

The system generally comprises a probe, such as, catheter 56, a spectrometer 40, and analyzer 42.

In more detail, the catheter 56 includes an optical fiber or optical fiber bundle. The catheter 56 is typically inserted into the patient 2 via a peripheral vessel, such as the femoral artery 10. The catheter head 58 is then moved to a desired target area, such as a coronary artery 18 of the heart 16 or the carotid artery 14. In the embodiment, this is achieved by moving the catheter head 58 up through the aorta 12.

When at the desired site, radiation is generated. In the current embodiment optical illuminating radiation is generated, preferably by a tunable laser source 44 and tuned over a range covering one or more spectral bands of interest. In other embodiments, one or more broadband sources are used to access the spectral bands of interest. In either case, the optical signals are coupled into the optical fiber of the catheter 56 to be transmitted to the catheter head 58.

In the current embodiment, optical radiation in the near infrared (NIR) spectral regions is used for spectroscopy. Exemplary scan bands include 1000 to 1450 nanometers (nm) generally, or 1000 nm to 1350 nm, 1150 nm to 1250 nm, 1175 nm to 1280 nm, and 1190 nm to 1250 nm, more specifically. Other exemplary scan bands include 1660 nm to 1740 nm, and 1630 nm to 1800 nm. In some implementations, the spectral response is first acquired for a full spectral region and then bands selected within the full spectral region for further analysis.

However, in other optical implementations, scan bands appropriate for fluorescence and/or Raman spectroscopy are used. In still other implementations, scan bands in the visible or ultraviolet regions are selected.

In the current embodiment, the returning, diffusely reflected light is transmitted back down the optical fibers of the catheter 56 to a splitter or circulator 54 or in separate optical fibers. This provides the returning radiation or optical signals to a detector system 52, which can comprise one or multiple detectors.

A spectrometer controller 60 monitors the response of the detector system 52, while controlling the source or tunable laser 44 in order to probe the spectral response of a target area, typically on an inner wall of a blood vessel and through the intervening blood or other unwanted signal source, which is typically a fluid.

As a result, the spectrometer controller 60 is able to collect spectra. When the acquisitions of the spectra are complete, the spectrometer controller 60 then provides the data to the analyzer 42.

With reference to FIG. 1B, the optical signal 20 from the optical fiber of the catheter 56 is directed by a fold mirror 62, for example, to exit from the catheter head 58 and impinge on the target area 22 of the artery wall 24. The catheter head 58 then collects the light that has been diffusely reflected or refracted (scattered) from the target area 22 and the intervening fluid and returns the light 102 back down the catheter 56.

In one embodiment, the catheter head 58 spins as illustrated by arrow 110. This allows the catheter head 58 to scan a complete circumference of the vessel wall 24. In other embodiments, the catheter head includes multiple emitter and detector windows, preferably being distributed around a circumference of the catheter head 58. In some further examples, the catheter head 58 is spun while being drawnback through the length of the portion of the vessel being analyzed.

However the spectra are resolved from the returning optical signals 102, the analyzer 42 makes an assessment of the state of the blood vessel wall 24 or other tissue of interest and, specifically area 22 that is opposite the catheter head 58, from collected spectra. The collected spectral response is used to determine whether the region of interest 22 of the blood vessel wall 24 comprises a lipid pool or lipid-rich atheroma, a disrupted plaque, a vulnerable plaque or thin-cap fibroatheroma (TCFA), a fibrotic lesion, a calcific lesion, and/or normal tissue in the current application. In another example, the analyzer makes an assessment as to the level of medical risk associated with portions of the blood vessel, such as the degree to which portions of the vessels represent a risk of rupture. This categorized or even quantified information is provided to an operator via a user interface 70, or the raw discrimination or quantification results from the collected spectra are provided to the operator, who then makes the conclusion as to the state of the region of interest 22.

In one embodiment the information provided is in the form of a discrimination threshold that discriminates one classification group from all other spectral features. In another embodiment, the discrimination is between two or more classes from each other. In a further embodiment the information provided can be used to quantify the presence of one or more chemical constituents that comprises the spectral signatures of a normal or diseased blood vessel wall.

In therapeutic applications, the returning optical signals are used to control the therapy, such as the level and pulse period of a delivered beam, such as for ablation.

As discussed previously, however, one problem that arises is the relative motion between the catheter head 58 and the vessel wall 24. Movement in the catheter head 58 is induced by heart and respiratory motion. Movement in the catheter head 58 is also induced by flow of the intervening fluid 108, typically blood. The periodic or pulse-like flow causes the catheter head 58 to vibrate or move as illustrated by arrow 104. Further, the vessel or lumen are also not static. There is motion, see arrow 106, in the vessel wall 24 adjacent to the catheter head 58. This motion derives from changes in the lumen as it expands and contracts through the cardiac cycle. Other motion could be induced by the rotation 110 of the catheter head 58. Thus, the relative distance between the optical window 48 of catheter head 58 and the region of interest 22 of the vessel 24 is dynamic, but somewhat correlated to the cardiac cycle.

The changes in the distance between the catheter head and the target area 22 affect the degree to which the system 50 can assess or treat the target area 22. In therapeutic applications, increases in the distance decrease the intensity of the optical signal received at the target area 22 due to absorption by the blood. In diagnostic applications, such as spectroscopy, increases in the distance decrease the degree to which the received optical signals are characteristic of the target area 22.

Figure 2:
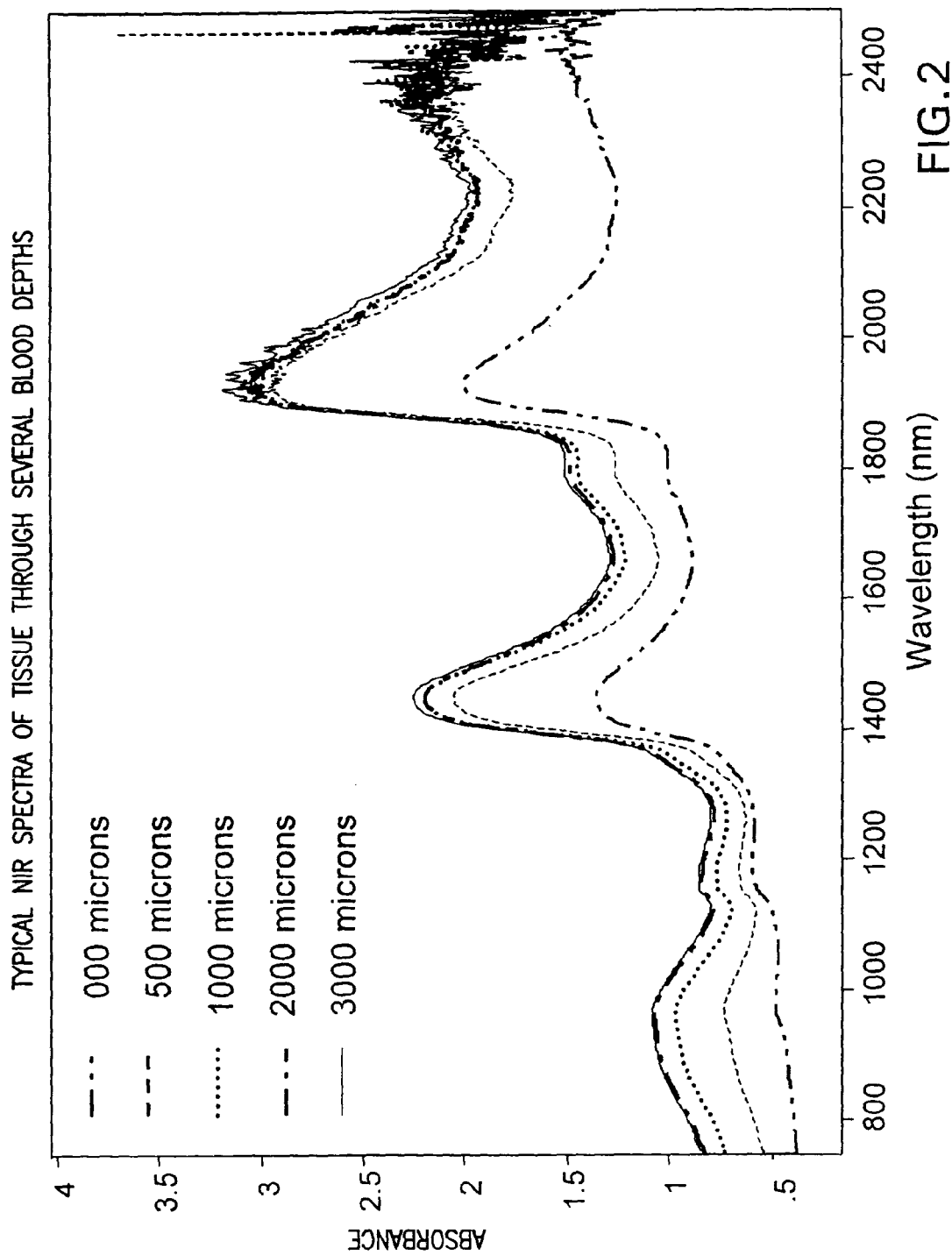
FIG. 2 is a plot of absorbance as a function of wavelength showing typical spectra for vessel tissue for several blood depths.

For example, FIG. 2 is a plot of absorbance as a function of wavelength. It shows a characteristic NIR spectrum for blood and vessel tissue. The different data sets were collected at several blood depths. As illustrated, depending on the distance between the catheter head 58 and the target area of the blood vessel wall 22, the collected spectra show a substantial degree of variation. Generally, as the distance between the catheter head increases from 1 to 3 millimeters, for example, the collected spectra become progressively more "bloodlike". As a result, it is more difficult to resolve the spectral contribution from the vessel walls, and therefore, make an assessment as to the state of those vessel walls, even with robust chemometric algorithms. This figure also illustrates that in the case of an absorbance spectra, the signal of the plaque is typically less than a threshold set for the blood spectrum.

FIG. 1C illustrates an example of an image generated and provided to the operator via a monitor of the user interface 70 in which an indication of the distance between the catheter head 58 and the target area 22 is provided.

In this example, the round circle 71 represents chemometric prediction values as catheter 56 examines a circumference of the vessel.

The vessel assessment map 72 comprises a series of circles or pixels, acquired as catheter 56 traverses some length of artery while spinning to thereby acquire data from the entire vessel's circumference for the length. Specifically, the horizontal axis is vessel position in millimeters, and the vertical axis is circumferential position in degrees.

A color line scale 73 shows the relationship between color or shade or pattern at each pixel of the vessel assessment map 72 and a chemometric prediction value based on the acquired spectral data. In one example, the scale represents an increasing risk of rupture moving left to right. In the preferred embodiment a continuous color scale is used to illustrate increasing risk of rupture. This scale is used by the operator to identify regions of the vessel wall representing a high risk of rupture by reference to the vessel assessment map 72.

The pixels of proximity or "blood-like" map 74 correspond to the same pixels of the assessment map 72 and thus the same locations of the vessel wall. The proximity map 74 provides an indication of the closeness of the catheter head 58 to the vessel wall, when the spectral data were captured. In the illustrated map, the darker colors represent locations where catheter is farther from the wall, thus making the captured spectral response increasingly more blood-like. As the spectral response becomes more blood-like, there is a concomitant decrease in the accuracy or confidence in the corresponding chemometric prediction value in the vessel assessment map 72.

Figure 3A:
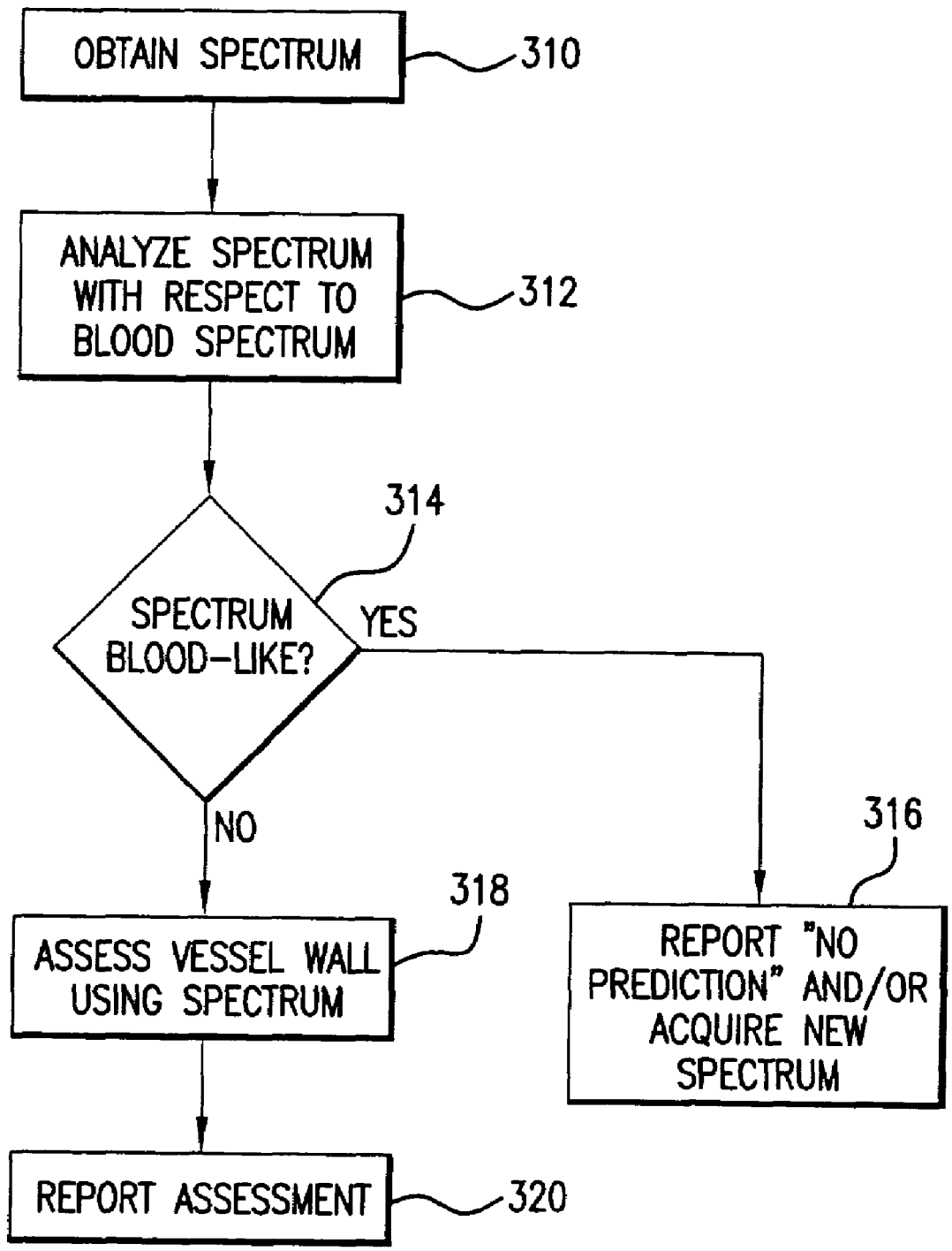

FIG. 3A shows a method for optically examining blood vessel walls to address this relative motion and improve the contribution of the tissue of interest in the collected spectra, according to the principles of the present invention.

Specifically, the spectrum is obtained in step 310. In the preferred embodiment, this includes first generating optical signals with the source 44. The optical signals are received back from the region of interest 22 and detected by the detector system 52. The time varying response, in the case of a tunable laser or tunable detector type system, is then resolved into the spectrum for the received optical signals 102. This spectrum is then analyzed relative to the spectral response of blood in step 312.

According to one method, the collected spectrum is compared to a stored blood-only spectrum. In one implementation, the collected spectrum is compared to the "infinite blood spectrum" using, for example, a typical spectral comparison method such as a sum of the squared differences of the absorbance at each wavelength.

This blood-only or "infinite blood spectrum" is collected for each patient, in one embodiment. This is accomplished in one example by placing a sample of the patient's blood in a blood reference well. Typically, this provides at least 3 millimeters (mm) of blood, or even or 5 mm or 10 mm of blood surrounding the catheter head 58 on all sides. The resulting collected spectra are thus the infinite spectra of the blood. In another embodiment, the blood-only spectrum is acquired by placing the catheter or probe within the patient in area that has a large distance between the probe and the vessel wall, such as the aorta, for example, or other large blood vessel.

In another implementation, algebraic techniques are used to analyze the collected spectrum to determine if it is blood-like. This implementation is especially applicable when performing spectroscopy in the ultraviolet, visible, or 600 to 1000 nm wavelength range, but can be used with any set of wavelengths where the spectral features of blood are known. This is accomplished, in one example, by identifying known feature or features, e.g., peaks and troughs, in the blood spectra. One example of a peak exists at 980 nm and a trough is usually present around 1300 nm, see FIG. 2, 3000 micron data. The ratio of the absorbances at these two wavelengths can be used as an indicator of whether the spectrum was blood-like. Alternately, the difference in the absorbances at these two wavelengths could be used as an indicator. In a still further example, the slope of the spectra on either side of a known blood peak may be used as the indicator. In the visible range and 600 to 1000 nm wavelength range, the known blood spectra would be oxygenated blood, enabling reference to the features of water or oxygenated hemoglobin to determine whether the spectra was blood-like. Other algebraic indicators could also be derived from known spectral features of blood to indicate whether a spectrum is blood-like.

A second method of comparing the collected spectrum to blood includes building a chemometric discrimination model using a larger population of patients. This discrimination model is preferably built using blood-only spectra from all patients (e.g. principle component analysis using Mahalanobis distance (PCA-MD) or such as with the embedded spectral residuals in PCA-MDR). A multi-class classification model can also be used in an embodiment that might assess blood-only and tissue-through-blood spectra from all patients (e.g. partial least squares discriminant analysis (PLS-DA), decision trees applied to PCA algorithms, etc.).

Other classification techniques (e.g. decision trees, neural nets or support vector machines, etc.) can alternatively be used. The model provides class membership of the spectra (blood-only vs. tissue through blood) or an index (real number), which is interpreted by a program or operator. The index is the calculated outcome of the prediction algorithm prior to the discrimination step, which compares the index to a pre-set threshold.

These classification models discriminate or filter out blood-only spectra from spectra that contain signal of tissue through blood. For example, spectra are acquired of fresh human tissue under various depths of blood, as well as infinite blood, for one or more patients. A chemometric classification model is then built. New spectra are then predicted with this model and filtered out if they are too similar to the blood group.

The acquired spectra are first evaluated for their closeness to blood-only. For example, the discriminant (e.g. the DA of PLS-DA) creates a scale that at one extreme indicates blood-only and at the other extreme indicates mostly-tissue. A threshold is set to either reject the spectral reading or to accept the spectral reading and perform chemometric tissue type evaluation. The threshold could be adjusted to optimize the performance of the chemometric algorithm. For example, if the chemometric algorithm performed poorly, then the threshold could be set to exclude more spectra that are closer to the blood-only set of spectra. Another example is PCA-MDR, which is based upon the application of a ellipsoidal-shaped region around the results of the blood-only samples. The "threshold" is based upon the number of standard deviations away from the centroid of the regions. It is not a linear threshold.

In order to confirm the ability of discriminant analysis to identify blood-only spectra and thus indirectly determine the catheter's position relative to the vessel wall, ten catheters were used to collect spectra of a standard target under varying depths of blood (0000 to 5000 micrometers). Spectra from 4500 and 5000 micrometers of depth were considered as "blood only." Chemometric models were built to classify spectra into "blood like" or "not blood like." The discrimination algorithm used was PCA-MDR. Pre-processing techniques were either: 1) multiplicative scatter correction and mean centering (MSC+MC); or 2) standard normal variance and mean centering (SNV+MC). The number of PCA factors for the model was selected to optimize prediction results without overfitting. Subsets of the overall wavelength range were analyzed to optimize prediction results.

The following tables show results for four models built using both the 4500 micrometer and 5000 micrometer data files.

TABLE 1

Percentage of files predicting as "blood like" at each blood depth using wavelengths from 1195 nanometers to 1275 nanometers and MSC + MC.

| MSC MC | 1195-1275 | | | | | | | | | |
|---|---|---|---|---|---|---|---|---|---|---|
| | 0000 | 0500 | 1000 | 1500 | 2000 | 2500 | 3000 | 3500 | 4000 | Factors |
| SINGLE | 0 | 0 | 0 | 30 | 80 | 80 | 80 | 70 | 80 | F2 |

TABLE 2

Percentage of files predicting as "blood like" at each blood depth using wavelengths from 1200 nanometers to 1273 nanometers and MSC + MC.

| | 1200-1273 | | | | | | | | | |
|---|---|---|---|---|---|---|---|---|---|---|
| MSC MC | 0000 | 0500 | 1000 | 1500 | 2000 | 2500 | 3000 | 3500 | 4000 | Factors |
| SINGLE | 0 | 0 | 0 | 50 | 80 | 100 | 90 | 70 | 100 | F2 |

TABLE 3

Percentage of files predicting as "blood like" at each blood depth using wavelengths from 1195 nanometers to 1275 nanometers and SNV + MC.

| | 1195-1275 | | | | | | | | | |
|---|---|---|---|---|---|---|---|---|---|---|
| SNV MC | 0000 | 0500 | 1000 | 1500 | 2000 | 2500 | 3000 | 3500 | 4000 | Factors |
| SINGLE | 0 | 0 | 0 | 60 | 80 | 90 | 90 | 80 | 90 | F2 |

TABLE 4

Percentage of files predicting as "blood like" at each blood depth using wavelengths from 1200 nanometers to 1273 nanometers and SNV + MC.

| | 1200-1273 | | | | | | | | | |
|---|---|---|---|---|---|---|---|---|---|---|
| SNV MC | 0000 | 0500 | 1000 | 1500 | 2000 | 2500 | 3000 | 3500 | 4000 | Factors |
| SINGLE | 0 | 0 | 0 | 50 | 70 | 100 | 100 | 100 | 100 | F1 |

In summary, at blood depths of 0000, 0500, and 1000 micrometers, spectra were recognized as not blood like. At 4000 micrometers, spectra were typically recognized as blood like. Table 4 shows good results at intermediate depths, with spectra acquired at 2500 micrometers or more blood depth being classified as mostly blood, and spectra acquired at 0 to 1000 micrometers being classified as not-blood. Thus, discriminant analysis is able to identify blood-only spectra and thus indirectly determine a relative position of the catheter to the vessel wall.

As an alternative to the filter or screening step, all spectra are measured by the chemometric tissue type algorithm, and the results of that step are reported to the operator with the results of the difference from blood-only. In this way, operators interpret the data more directly. This is shown in FIG. 1C.

In still another method, a quantitative analysis of the spectrum is performed to determine whether the spectral signal is the product of a spectrum captured or acquired when the catheter head is too far from the vessel wall. In one example, Partial Least Squares (PLS) chemometric analysis is used to determine the quantitative percentage of blood in the volume being spectrally sampled. Then, a threshold is set, and samples are rejected if the percentage of blood was too high. Alternately, instead of rejecting the spectra, both the evaluation of the sample and the percentage of blood are reported to the operator.

Other quantitative chemometric techniques, such as Linear Regression, Classical Least Squares, Inverse Least Squares, Principal Components Regression or other techniques can also be used. Instead of a quantitative percentage of blood, an absolute amount of blood is measured in still further embodiments.

In other embodiments, the spectra of the received optical signals 102 are analyzed relative to some other metric, instead of blood-based spectra, to determine distance from the vessels walls. One such metric is the expected spectral response of the vessels walls in either a normal or diseased state, for example.

In step 314, it is determined whether the spectrum is too blood-like and that the catheter head is too far from the vessel wall based on the analysis step 312. Step 314 can be performed automatically by the analyzer 42 or by the operator after observation of the data provided by the analyzer 42. If the spectrum is blood-like, then it is assumed that the catheter head 58 is not close enough to the vessel walls to enable assessment of the vessel walls. A report of no prediction and/or an instruction to acquire new spectra are then generated in step 316.

To implement this technique in vivo, many spectral readings are preferably acquired at a single position in the axial direction of the artery or blood vessel during at least one, and typically over multiple, cardiac cycles. Alternatively, the difference between the spectra and blood can be reported to the operator along with the spectral reading, so the operator can decide whether to accept the spectral reading. Furthermore the difference between the spectra and blood can be used to ignore that spectrum and the catheter will automatically remain in position until a preset number of non-blood-like spectra are collected at that location.

Another variation is to apply this technique to a rotating catheter. A series of readings are taken and the catheter orientation tracked over time. In one example, the catheter head rotates at 4 Hertz. Then, each time the catheter returns to the same orientation, one or more spectral readings are acquired, thus simulating the acquisition of many spectral readings at a single position. These steps are sometimes combined with other simultaneous operations to evaluate the length of vessel. That is, the catheter is initially placed at the distal point of the portion to be evaluated, and then pulled back through the vessel until the desired area is evaluated. Pullback is usually done via a motorized system to make it easy for the operator. Repeated pullbacks of the same vessel are usually performed, by manually returning the catheter to the same starting location. However, in other implementations, the catheter is not rotated during these pullbacks, if desired by the operator.

For the spectra that are determined to be acceptable, e.g., sufficiently non blood-like, it is assumed that the catheter head is close enough to the vessel walls to enable assessment of the vessel walls. Thus, the assessment is made of the vessel walls using the spectra or spectrum in step 318.

In the embodiments, this assessment of the vessel walls is performed as described in U.S. patent application Ser. No. 10/426,750, filed on Apr. 30, 2003 (entitled "Spectroscopic Unwanted Signal Filters for Discrimination of Vulnerable Plaque and Method Therefor", by Barbara J. Marshik-Geurts and Huwei Tan) or U.S. patent application No. 10/212,845, filed Aug. 5, 2002 (entitled "Near-Infrared Spectroscopic Analysis Of Blood Vessel Walls", by Barbara Marshik-Geurts, Jing Tang, and Andres Zuluaga), the teachings of these applications being incorporated herein by this reference in their entirety.

Finally, in step 320, a report of the assessment is generated to the operator. Data and/or results are most commonly displayed on a computer screen, but may also be printed out. Audio signals and optical signals (e.g. control panel light emitting diodes) and other methods may be used.

Figure 3B:
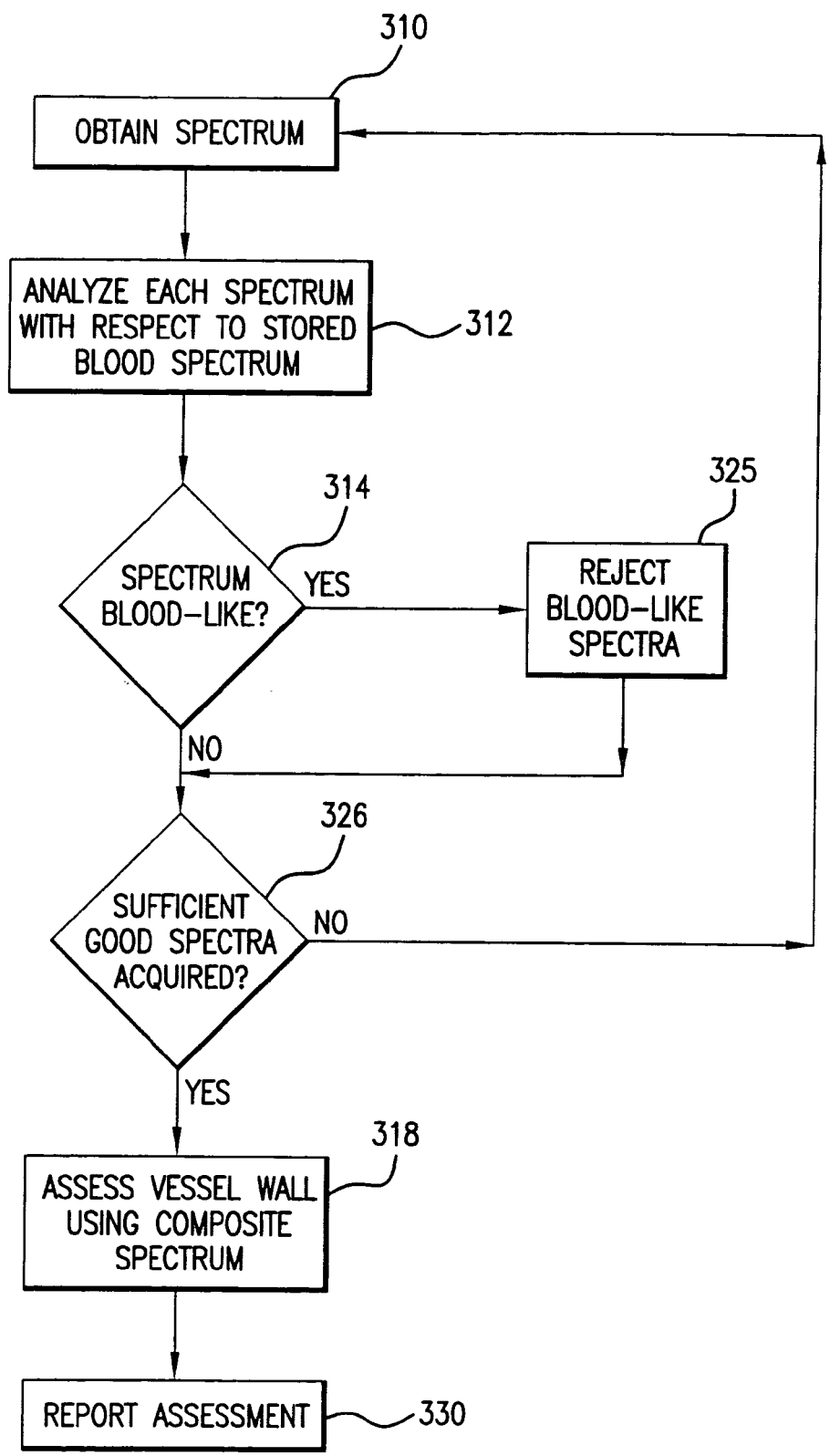
FIG. 3B is a flow diagram showing a method for blood vessel analysis according to another embodiment of the present invention that creates a composite spectrum of non-blood like spectra.

FIG. 3B shows another embodiment of the method for optically examining blood vessel walls in the presence of motion. This embodiment uses a composite or average spectrum from a number of acquisitions.

In more detail, in step 310, a spectrum is obtained as described previously. Then, the spectrum is analyzed with respect the spectral components of blood or as described previously relative to step 312 of FIG. 3A. In step 314, it is determined whether the spectrum is blood-like, or not, i.e., whether the catheter head is sufficiently close to the vessel wall.

If the spectrum is blood-like, then it is rejected in step 325. Then, in step 326, an assessment is made as to whether or not there are sufficient good spectra acquired yet. If adequate spectra have not been acquired, then the processing returns to step 310 to acquire a new spectrum. Generally, in some embodiments, a set number such as five or ten good spectra are acquired before processing continues through step 326.

In some cases, it is necessary to average only spectra that were acquired under the same noise conditions, i.e., have the same signal to noise ratios. Generally, random noise from separate acquisitions will average to zero for the same noise levels. Thus, in one implementation, spectra acquired at the same relative proximity to the vessel walls are averaged, rather then simply the spectra acquired at the closest proximity to the vessel walls. Thus, the proximity assessment is used to minimize the proximity variation between the acquired spectra that are averaged.

Once enough spectra are acquired, as determined in step 326, an assessment is made of the vessel walls, using a composite spectrum, in step 318. This step is generally the same as the similar step described with reference to FIG. 3A. In one example, the spectrum that is used for the assessment is an average of the acquired, good spectra that are applied to a model based upon the same number of averaged "good model spectra".

Note that generally when using a chemometric model, the same numbers of averages in both the "Blood Filter" and in the "Prediction Model" are required in order for the algorithms to work. This impacts signal to noise ratio.

Then, a report of the assessment is generated in step 330.

The composite spectrum embodiment has the advantage using a composite spectrum collected over time. This reduces problems associated with poor signal quality associated with a single acquisition.

Figure 4:
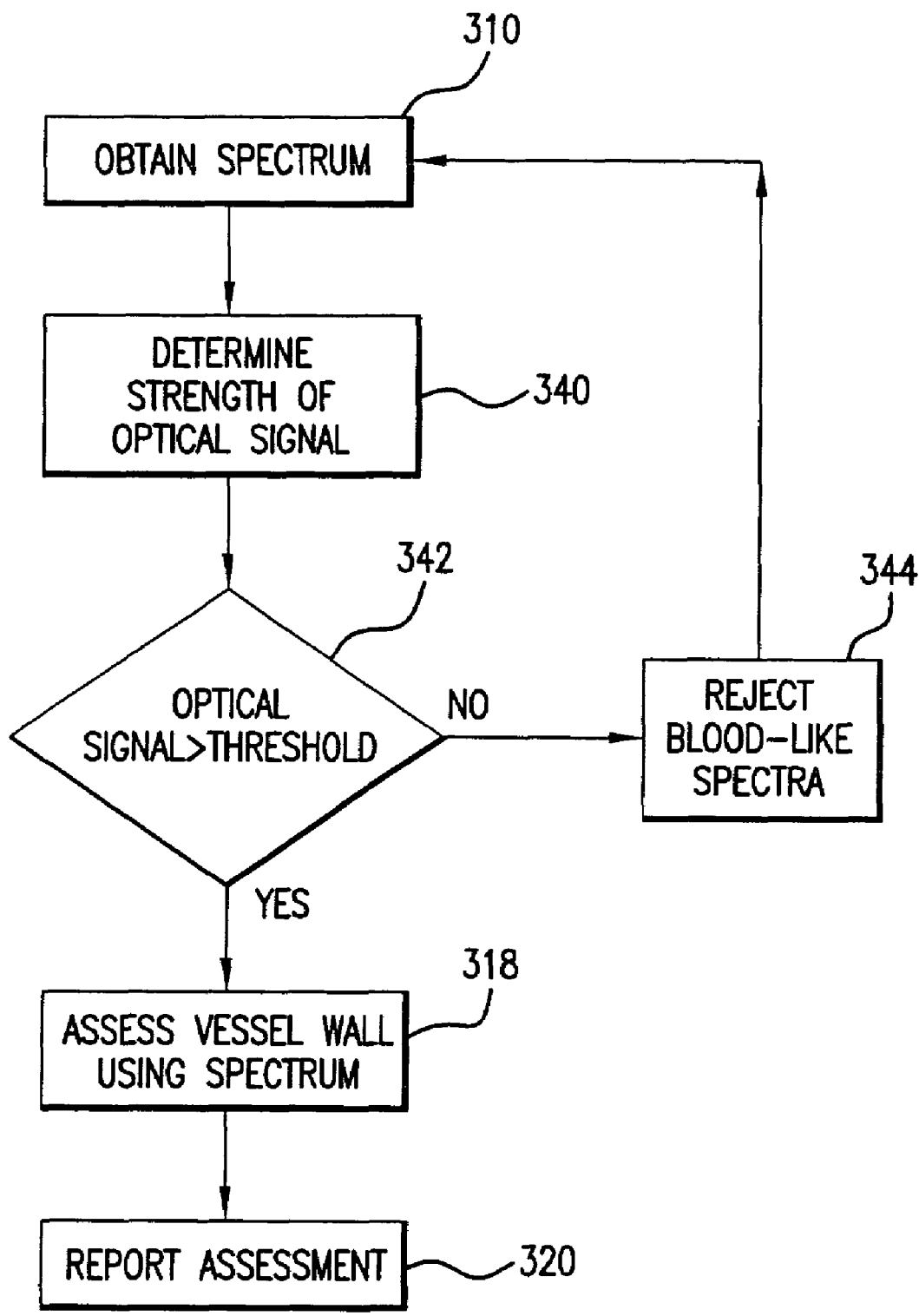
FIG. 4 is a flow diagram showing a method for blood vessel analysis according to still another embodiment of the present invention that determines whether the spectra are blood-like with reference to the optical signal amplitude or raw optical signal that is detected by the detector.

FIG. 4 illustrates still another embodiment of the present invention that relies on returning signal amplitude to determine the distance between the catheter head and the vessel wall.

Here again, spectra are acquired in step 310. Then, in step 340, the strength of the optical signals is determined. Generally, it had been found that the strength of the returning optical signal varies as a function of the distance between the catheter head 58 and the target area 22 of the vessel walls. Generally, the signal strength increases as the catheter head 58 gets closer to the vessel walls 24. This co-variant relationship between blood depth and total light returned has been observed across all tissue types. That is, the closer the head 58 is to the vessel wall, the more light is received overall. This effect is a function of absorption and scattering properties of blood and vessel wall, and a function of the probe (light emitting and collecting) geometry.

Consequently, in one embodiment, if the probe continuously emits and receives light at a fixed wavelength or in a waveband, it is possible to determine the times when the catheter head or probe 58 is at the minimum and maximum distances from the wall, by looking at the minimum and maximum of the total light returned for each spectra. While these data can be used to provide an accurate absolute measure of depth, only a relative measurement of depth is typically required.

When the amplitude of the optical signal, i.e., raw optical signal measured by the detector system 52, is greater than a fixed or adaptive threshold in step 342, the spectrum is acquired and then used to assess the vessel walls in step 318, as described previously. In the case where the assessment is based on absorbance units, the spectrum is acquired and then used when the absorbance spectrum is less than the fixed or adaptive threshold in step 342. The blood adsorbs the signal to a greater degree than the tissue. Thus the absorbance value of blood that is generated is higher than those from the signal of tissue (see the spectra in FIG. 2). The report is then generated in step 320.

Spectral readings at or around the minimum depth, i.e., when the most light is detected, will include a higher contribution of vessel wall to the spectrum. Using these readings will improve the overall signal-to-noise of the system. In other words, overall system detection abilities are improved by eliminating measurements when the system's response is weakest.

It should be noted, however, that this co-variant relationship between blood depth and total light returned was not observed with all catheter optics, because the phenomenon does depend on the probe configuration.

In the previously described operation of the invention, the periods when the optical signal is analyzed to assess the vessel walls, is judiciously selected by indirectly monitoring the changes in the distance between the catheter head 58 and the target area 22. In this way, the invention achieved improved performance due to catheter movement, a characteristic that has been viewed as undesirable in some prior art designs.

According to one modification, the catheter is designed or configured to actually increase its movement during operation. As the travel increases, there is an increased ability to capture the optical signal at the moments when the catheter head 58 is especially close to the vessel walls to thereby further improve the signal to noise ratio by minimizing the pathlength through the fluid or blood 108.

Figure 5:
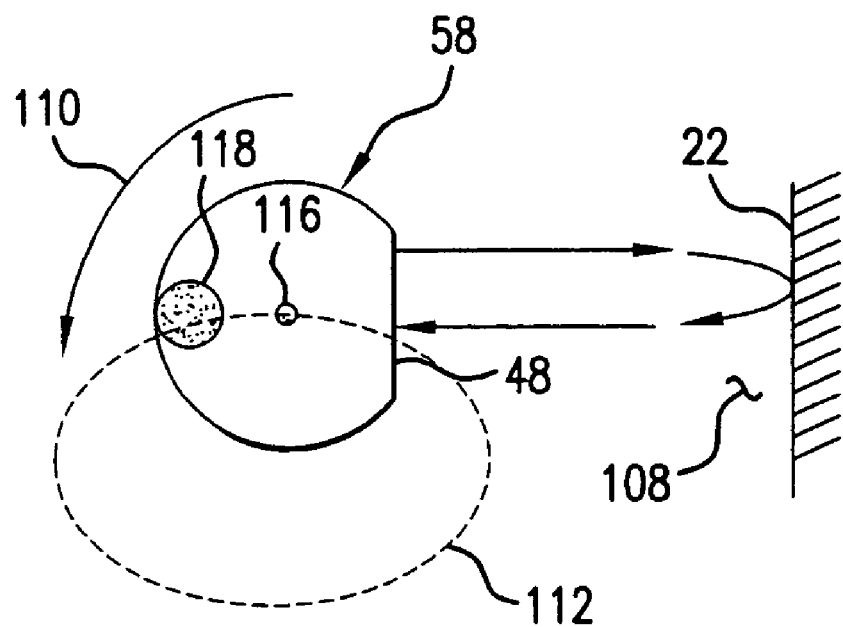
FIG. 5 is a schematic top plan view of a catheter head with an eccentric weight to induce motion according to the present invention.

FIG. 5 shows a first embodiment of the catheter providing for increased movement during operation.

The catheter head 58 includes a high density mass or weight 118 that is located away from the axis of rotation 116 for the catheter head 58. As a result, when the catheter 56 is driven to rotate, see arrow 110, the catheter head 58 traces an elliptical path 112. This elliptical path 112 brings the optical window 48 of the catheter head 58 into close proximity with the target 22. By timing the capture of the optical signal and assessment of the vessel walls with the point in time when the elliptical path 112 of the catheter head 58 brings the optical window 48 in proximity to the target area 22, the signal to noise is maximized.

As discussed previously, this rotation is sometimes combined with other simultaneous operations, as described previously, in which catheter head 58 is initially placed at the distal point of the vessel portion to be evaluated, and then pulled back through the vessel until the desired area is evaluated.

Figure 6A:
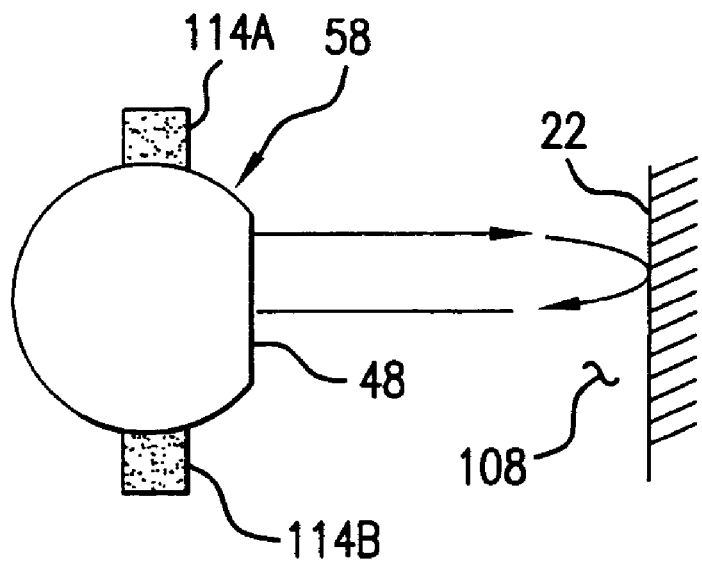
FIGS. 6A and 6B are a schematic top and side plan views of a catheter head according to another embodiment that uses wings to induce motion according to the present invention.
Figure 6B:
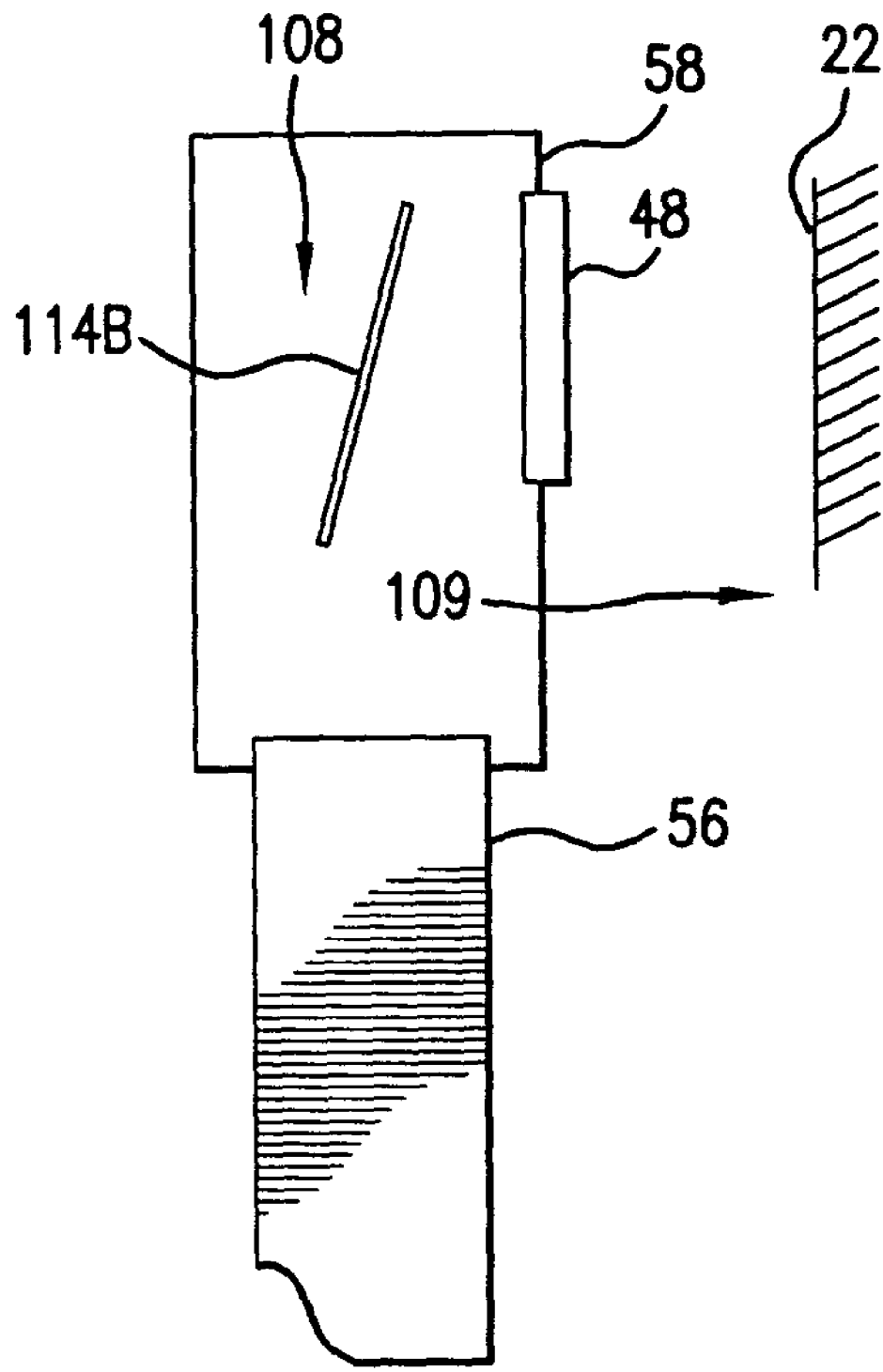

FIGS. 6A and 6B show a second embodiment of the catheter providing for increased movement during operation.

Referring to 6A, here the catheter head 58 includes right and left wings or fins 114A and 114B. These wings or fins 114A, 114B interact with the flowing blood 108 to cause the catheter head to move relative to the target area 22. This causes the optical window 48 to periodically move closer to the target area 22 to enable high signal to noise analysis of the target area 22 by reducing the pathlength through the blood 108.

In the specific embodiment, the wings 114A, 114B are angled relative to the centerline of the catheter head 58 as shown in FIG. 6B. Here the flowing blood 108 acts on the wings 114 to push the catheter head 58 in a direction that is orthogonal to the optical window 48, in the direction of the target area 22. Thus, as the flow rate of the blood 108 increases, the catheter head is moved closer to the target area 22.

Generally, the wings may be designed according to well known techniques in aeronautical engineering and fluid dynamics. In particular, computation fluid dynamics (CFD) allows the design and simulation of wings to achieve desired motion characteristics.

In other embodiments, multiple sets, or pairs, of wings are installed or formed on the catheter head 58. One of set of these wings is designed to cause the catheter head 58 to oscillate back and forth from the wall 24 in a first radial direction, such as in a direction that is orthogonal to the optical window of 48 catheter head 58. Another set of wings is used to cause the catheter head 58 to oscillate back and forth from the wall in a second radial direction, which is perpendicular to the first radial direction.

In still another embodiment, the wings are designed to move the catheter head towards the wall in one direction when blood flow is slower, and move the catheter towards the opposite wall when the blood flow is faster.

In the embodiments in which the catheter head's movement is correlated to the blood flow rate, ecg gating is preferably used to time the acquisition of the spectral response of the target area 22. In some embodiments ecg gating is used in addition to analysis of the received optical signals as described previously.

Figure 7A:
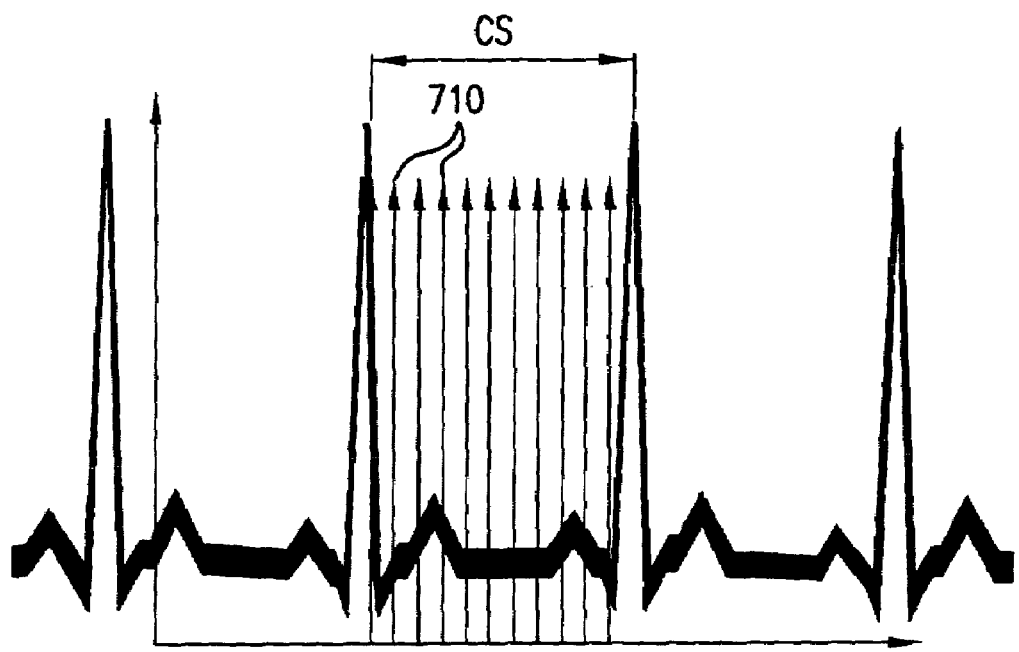
FIGS. 7A and 7B are timing diagrams showing the timing for optical signal capture during cardiac cycles according to the invention.
Figure 7B:
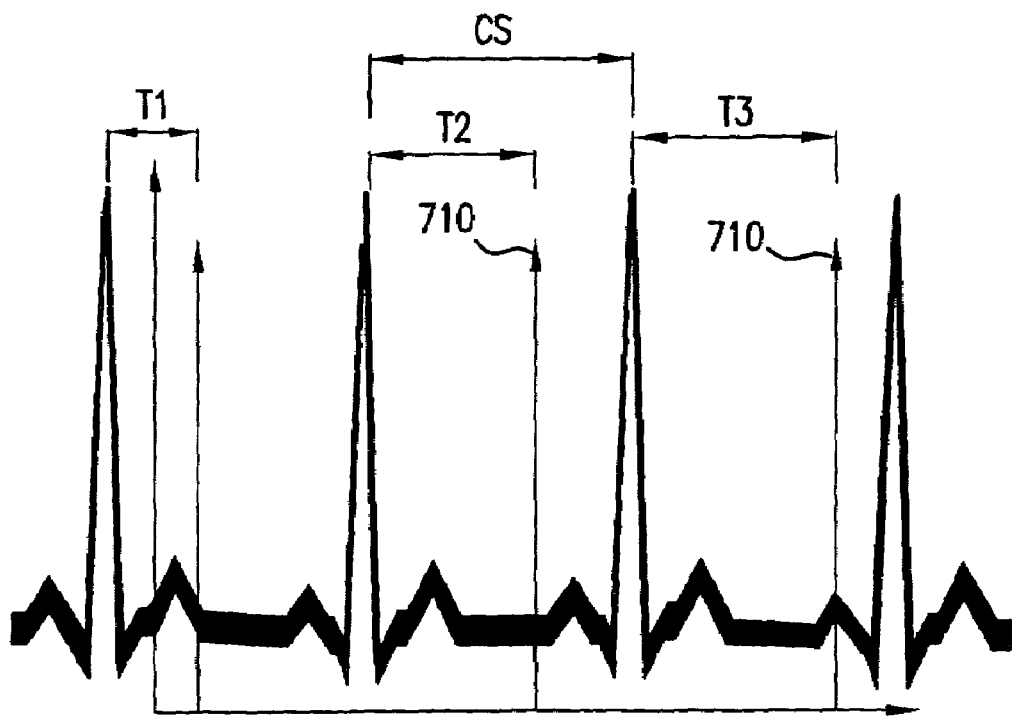

FIGS. 7A and 7B illustrate two embodiments of the ecg gating.

In FIG. 7A, the optical signals are spectrally analyzed at several points 710 in the cardiac cycle CS. This enables the system to find the point in the cardiac cycle when the flow characteristics are such that the catheter head 58 is in the optimal relationship to the target area 22.

The embodiment of FIG. 7A, however, requires a relatively high speed system. In another embodiment illustrated in FIG. 7B, the spectral analysis is performed over several cardiac cycles but at different delays from the start of the cycles, T1, T2, T3, . . . TN. This system enables lower processing requirements, yet is still able to find the optimal portion of the cycle for analysis.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for optically examining vessel walls of a blood vessel with a probe through intervening fluid, the method comprising:
    inserting the probe into the blood vessel;
    generating optical signals with the probe and directing the optical signals to the vessel walls;
    receiving optical signals from the vessel walls through the intervening fluid at the probe;
    analyzing the received optical signals to perform a proximity analysis to determine whether the probe is close enough to the vessel walls to enable assessment of the vessel walls by comparison of the received optical signals to a reference relating to a known characteristic of said intervening fluid; and
    using the received optical signals to assess the vessel walls using spectral analysis of the optical signals when the probe is determined to be close enough to the vessels walls from the proximity analysis to enable the assessment of the vessel walls by the spectral analysis.

2. A method as claimed in claim 1, wherein the step of analyzing the optical signals for the proximity analysis comprises determining an amplitude of the optical signals.

3. A method as claimed in claim 2, wherein the step of analyzing the optical signals to determine whether the probe is close to the vessel walls for the proximity analysis comprises comparing the amplitude of the received optical signals to a threshold and the step of using the received optical signals to assess the vessel walls for the spectral analysis is performed if the amplitude of the received optical signals is within the requirements of the threshold.

4. A method as claimed in claim 1, wherein the step of using the received optical signals to assess the vessel walls for the spectral analysis comprises assessing the vessel walls in response to the spectral response of the vessel walls.

5. A method as claimed in claim 1, wherein an operator determines whether to use the received optical signals to assess the vessel walls based on a result of the step of analyzing the optical signals.

6. A method as claimed in claim 1, wherein the step of analyzing the optical signals for the proximity analysis comprises comparing the optical signals to a spectral response of the intervening fluid and the step of using the received optical signals to assess the vessel walls for the spectral analysis is performed if the optical signals are sufficiently different from the spectral response of the intervening fluid.

7. A method as claimed in claim 6, wherein the intervening fluid is blood and the method further comprises acquiring the spectral response of the blood by extracting a sample of the patient blood and measuring the spectral response of the blood.

8. A method as claimed in claim 1, wherein the step of analyzing the optical signals for the proximity analysis comprises analyzing a spectral response of the optical signals based on spectral features of the intervening fluid.

9. A method as claimed in claim 8, wherein the intervening fluid is blood and the method further comprises comparing the spectral response of the optical signals to known spectral features of blood for the proximity analysis.

10. A method as claimed in claim 8, wherein the step of analyzing the optical signals comprises performing an algebraic analysis of the spectral response.

11. A method as claimed in claim 10, wherein the algebraic analysis comprises a ratiometric comparison of the spectral response at multiple wavelengths.

12. A method as claimed in claim 10, wherein the algebraic analysis comprises analyzing a difference in the spectral response at multiple wavelengths.

13. A method as claimed in claim 1, wherein the step of analyzing the optical signals for the proximity analysis comprises comparing the spectrum of the optical signals to the spectral response of the intervening fluid.

14. A method as claimed in claim 1, wherein the step of analyzing the optical signals to determine whether the probe is close enough to the vessel walls to enable assessment of the vessel walls for the proximity analysis comprises analyzing the optical signals using a chemometric model.

15. A method as claimed in claim 14, wherein the chemometric model is built from spectral responses of blood samples.

16. A method as claimed in claim 14, wherein the chemometric model is built from spectral responses of blood samples from a population of patients.

17. A method as claimed in claim 14, wherein the chemometric model is built from spectral responses of blood samples from a population of patients and augmented by a current patient blood spectrum or spectra.

18. A method as claimed in claim 1, wherein the step of receiving the optical signals comprises detecting the optical signals at multiple times during multiple cardiac cycles of the patient.

19. A method as claimed in claim 1, wherein the step of receiving the optical signals comprises detecting the optical signals at multiple times during a single cardiac cycle of the patient.

20. A method as claimed in claim 1, wherein the step of using the received optical signals to assess the vessel walls comprises averaging spectral responses from multiple points in time.

21. A method as claimed in claim 20, wherein the step of using the received optical signals to assess the vessel walls for the spectral analysis further comprises disregarding spectral responses that resemble a spectral response of the intervening fluid.

22. A method as claimed in claim 1, wherein the step of using the received optical signals to assess the vessel walls for the spectral analysis comprises averaging spectral responses from multiple times during a single or multiple cardiac cycles, if the spectral responses were collected when the probe was close enough to the vessel walls to enable assessment of the vessel walls.

23. A method as claimed in claim 1, wherein the step of using the received optical signals to assess the vessel walls for the spectral analysis comprises averaging spectral responses from multiple points in time if the spectral responses were collected when the probe was close enough to the vessel walls to enable assessment of the vessel walls.

24. A method as claimed in claim 1, further comprising inducing movement between the probe and the vessel walls.

25. A method for controlling diagnostic or therapeutic applications, the method comprising:
  inserting a probe into a blood vessel:
  generating optical signals with the probe and directing the optical signals to the vessel walls:
  receiving the optical signals from the vessel walls through intervening fluid at the probe;
  analyzing the received optical signals to perform a proximity analysis to determine whether the optical signals are indicative of the vessel walls and/or the intervening fluid by comparison of the received optical signals to a reference relating to a known characteristic of said intervening fluid;
  using the received optical signals to assess the vessel walls using spectral analysis of the optical signals when the probe is determined to be close enough to the vessels walls from the proximity analysis to enable the assessment of the vessel walls by the spectral analysis; and
  initiating diagnosis or treatment of the vessel walls in response to the step of analyzing the optical signals if the probe is determined to be close enough to the vessels walls to enable the diagnosis or treatment.

26. A method as claimed in claim 25, wherein in the step of analyzing the optical signals, the determination of whether the optical signals are indicative of the vessel walls and/or the intervening fluid is used to determine a proximity between the probe and the vessel walls.

27. A method as claimed in claim 25, wherein the step analyzing the optical signals for the proximity analysis comprises determining an amplitude of the optical signals.

28. A method as claimed in claim 25, wherein the step analyzing the optical signals for the proximity analysis comprises measuring an amplitude of the received optical signals and the step of initiating treatment is performed if the amplitude of the received optical signals is within the region designated as tissue signal with respect to a preset amplitude threshold.

29. A method as claimed in claim 25, wherein an operator determines whether to use the received optical signals to assess the vessel walls based on a result of the step of analyzing the optical signals.

30. A method as claimed in claim 25, wherein the step of analyzing the optical signals for the proximity analysis comprises comparing the optical signals to a spectral response of the intervening fluid and the step of initiating treatment is performed if the optical signals are sufficiently different from the spectral response of the intervening fluid.

31. A method as claimed in claim 30, wherein the intervening fluid is blood and the method further comprises acquiring the spectral response of the blood by extracting a sample of the patient blood and measuring the spectral response of the blood.

32. A method as claimed in claim 30, wherein the intervening fluid is blood and the method further comprises acquiring the spectral response of the blood by placing the catheter or probe within the patient in an area that has a large distance between the probe and the vessel wall.

33. A method as claimed in claim 25, wherein the step of analyzing the optical signals comprises analyzing a spectral response of the optical signals based on spectral features of the intervening fluid.

34. A method as claimed in claim 33, wherein the intervening fluid is blood and the method further comprises comparing the spectral response of the optical signals to known spectral features of blood.

35. A method as claimed in claim 33, wherein the step of analyzing the optical signals comprises performing an algebraic analysis of the spectral response.

36. A method as claimed in claim 35, wherein the algebraic analysis comprises a ratiometric comparison of the spectral response at multiple wavelengths.

37. A method as claimed in claim 35, wherein the algebraic analysis comprises analyzing a difference in the spectral response at multiple wavelengths.

38. A method as claimed in claim 25, wherein the step of analyzing the optical signals for the proximity analysis comprises comparing the spectrum of the optical signals to the spectral response of the intervening fluid.

39. A method as claimed in claim 25, wherein the step of analyzing the optical signals for the proximity analysis comprises analyzing the optical signals using a chemometric model.

40. A method as claimed in claim 39, wherein the chemometric model is built from spectral responses of blood samples.

41. A method as claimed in claim 39, wherein the chemometric model is built from spectral responses of blood samples from a population of patients.

42. A method as claimed in claim 39, wherein the chemometric model is built from spectral responses of blood samples from a population of patients augmented by a current patient blood spectrum or spectra.

43. A method as claimed in claim 25, wherein the step of receiving the optical signals comprises detecting the optical signals at multiple times during a single cardiac cycle of the patient.

44. A method as claimed in claim 25, wherein the step of assessing the vessel walls using the spectral analysis comprises averaging spectral responses from multiple points in time.

45. A method as claimed in claim 44, wherein the step of assessing the vessel walls using the spectral analysis comprises disregarding spectral responses that resemble a spectral response of the intervening fluid.

46. A method as claimed in claim 25, wherein the step of assessing the vessel walls using the spectral analysis comprises averaging spectral responses from multiple points in time if the spectral responses were collected when the probe was close enough to the vessel walls to enable assessment of the vessel walls.

47. A method as claimed in claim 25, wherein the step of assessing the vessel walls using the spectral analysis comprises averaging spectral responses from multiple times during a single cardiac cycle or multiple cardiac cycles if the spectral responses were collected when the probe was close enough to the vessel walls to enable assessment of the vessel walls.

48. A method as claimed in claim 25, further comprising inducing movement between the probe and the vessel walls.

49. A method for optically examining vessel walls of a blood vessel with a probe through intervening fluid, the method comprising:
 inserting the probe into the blood vessel:
 generating optical signals with the probe and directing the optical signals to the vessel walls:
 receiving optical signals from the vessel walls through the intervening fluid at the probe;
 analyzing the received optical signals indicative of a spectral response of the vessel walls to determine proximity information concerning a proximity between the probe and the vessel walls by comparison of the received optical signals to a reference relating to a known characteristic of said intervening fluid; and
 using the received optical signals to assess the vessel walls when the probe is determined to have a desired proximity to the vessels walls using spectral analysis.

50. A method as claimed in claim 49, wherein the proximity information is determined from a spectrum of the optical signals.

51. A method for optically examining vessel walls of a blood vessel with a probe through intervening fluid, the method comprising:
 inserting the probe into the blood vessel:
 generating optical signals with the probe and directing the optical signals to the vessel walls:
 inducing movement between the probe and the vessel walls;
 receiving optical signals from the vessel walls with the probe;
 determining whether the probe is close enough to the vessel walls to enable assessment of the vessel walls by comparison of the received optical signals to a reference relating to a known characteristic of said intervening fluid; and
 using the received optical signals to assess the vessel walls when the probe is determined to be close enough to the vessels walls using spectral analysis.

52. A method as claimed in claim 51, wherein the step of inducing movement between the probe and the vessels walls comprises configuring to the probe to interact with movement in an intervening fluid between the probe and the vessel walls.

53. A method as claimed in claim 51, wherein the step of determining whether the probe is close enough to the vessel walls comprises analyzing the optical signals.

54. A method as claimed in claim 51, wherein the step of analyzing the optical signals comprises spectrally analyzing the optical signals.

55. A system for examining vessel walls of a blood vessel, the system comprising:
 a probe configured to be inserted into the blood vessel for optically examining blood vessel walls by emitting optical signals and receiving optical signals from the vessel walls through intervening fluid;
 an optical source for generating the optical signals;
 a detector system for detecting the received optical signals from the vessel walls; and
 a controller for controlling the optical source and monitoring the response of the detector system to determine a spectral content of the optical signals from the vessel walls, the controller comparing the spectral content of the optical signals to a spectral response of the intervening fluid to perform a proximity analysis to determine whether the probe is close enough to the vessel walls to enable assessment of the vessel walls, the controller using the received optical signals to assess the vessel walls when the probe is determined to be close enough to the vessels walls to enable the assessment of the vessel walls using spectral analysis of the vessel walls.

56. A system as claimed in claim 55, wherein the controller uses the received optical signals to assess the vessel walls if the spectral content of the optical signals are sufficiently different from the spectral response of the intervening fluid.

57. A system as claimed in claim 56, wherein the intervening fluid is blood and the controller acquires the spectral response of the blood by measuring the spectral response of the blood.

58. A system as claimed in claim 56, wherein the controller analyzes the optical signals to determine whether the probe is close enough in the proximity analysis to the vessel walls to enable assessment of the vessel walls using a chemometric model.

59. A system as claimed in claim 58, wherein the chemometric model is built from spectral responses of blood samples.

60. A system as claimed in claim 58, wherein the chemometric model is built from spectral responses of blood samples from a population of patients.

61. A system as claimed in claim 58, wherein the chemometric model is built from spectral responses of blood samples from a population of patients and augmented by a current patient blood spectrum or spectra.

62. A system as claimed in claim 58, wherein the controller averages spectral responses from multiple times during a single or multiple cardiac cycles, if the controller determines that the optical signals were detected when the probe was close enough to the vessel walls to enable assessment of the vessel walls for the spectral analysis.

* * * * *

UNITED STATES PATENT AND TRADEMARK OFFICE
CERTIFICATE OF CORRECTION

PATENT NO. : 7,539,530 B2  Page 1 of 1
APPLICATION NO. : 10/646271
DATED : May 26, 2009
INVENTOR(S) : Caplan et al.

It is certified that error appears in the above-identified patent and that said Letters Patent is hereby corrected as shown below:

On the cover page, item [*] Notice: Subject to any disclaimer, the term of this patent is extended or adjusted under 35 USC 154(b) by 830 days Delete the phrase "by 830 days" and insert -- by 1293 days --

Signed and Sealed this

Eighth Day of June, 2010

David J. Kappos
*Director of the United States Patent and Trademark Office*